US00PP14181P29

(12) United States Plant Patent
Baumann et al.

(10) Patent No.: US PP14,181 P2
(45) Date of Patent: Sep. 30, 2003

(54) HYPERICUM PLANT NAMED 'BRIGHT BLOSSOM'

(50) Latin Name: *Hypericum androsaemum*
Varietal Denomination: Bright Blossom

(75) Inventors: Lauwers Baumann, Burgh Haamstede (NL); Sarah Cornelia Jonker, Burgh Haamstede (NL)

(73) Assignee: Maatschap Baumann - Jonker, Burgh Haamstede (NL)

( * ) Notice: Subject to any disclaimer, the term of this patent is extended or adjusted under 35 U.S.C. 154(b) by 0 days.

(21) Appl. No.: 10/232,889

(22) Filed: Aug. 31, 2002

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Hypericum plant named 'Bright Blossom', characterized by its upright and outwardly spreading plant habit; dark green-colored leaves; light red-colored fruits; and good postproduction longevity.

2 Drawing Sheets

Botanical classification/cultivar designation: *Hypericum androsaemum* cultivar Bright Blossom.

BACKGROUND OF THE INVENTION

The present Invention relates to a new and distinct cultivar of Hypericum plant, botanically known as *Hypericum androsaemum,* commercially used as cut stems with fruits, and hereinafter referred to by the name 'Bright Blossom'.

The new Hypericum was discovered and selected in June, 1998, by the Inventors in a controlled environment in Burgh Haamstede, The Netherlands, as a naturally-occurring whole plant mutation of the Hypericum cultivar Autumn Blaze, not patented. The new Hypericum was discovered within a population of plants of the cultivar Autumn Blaze and was selected on the basis of itslight red-colored fruits.

Asexual reproduction of the new Hypericum by terminal cuttings taken at Burgh Haamstede, The Netherlands since July, 1999, has shown that the unique features of this new Hypericum are stable and reproduced true to type in successive generations of asexual reproduction.

SUMMARY OF THE INVENTION

The following traits have been repeatedly observed and are determined to be the unique characteristics of 'Bright Blossom'. These characteristics in combination distinguish 'Bright Blossom' as a new and distinct cultivar:

1. Upright and outwardly spreading plant habit.
2. Dark green-colored leaves.
3. Light red-colored fruits.
4. Good postproduction longevity.

Plants of the new Hypericum differ primarily from plants of the parent cultivar in fruit coloration as plants of the cultivar Autumn Blaze have brown-colored fruits.

Plants of the new Hypericum can be compared to plants of the Hypericum cultivar Excellent Flair, not patented. In side-by-side comparisons conducted in Burgh Haamstede, The Netherlands, plants of the new Hypericum differed from plants of the cultivar Excellent Flair in the following characteristics:

1. Plants of the new Hypericum had darker green-colored leaves than plants of the cultivar Excellent Flair.
2. Plants of the new Hypericum had smaller fruits than plants of the cultivar Excellent Flair.
3. Plants of the new Hypericum had light red-colored fruits whereas plants of the cultivar Excellent Flair had brown-colored fruits.

BRIEF DESCRIPTION OF THE PHOTOGRAPHS

The accompanying colored photographs illustrate the overall appearance of the new Hypericum, showing the colors as true as it is reasonably possible to obtain in colored reproductions of this type. Colors in the photographs may differ slightly from the color values cited in the detailed botanical description which accurately describe the colors of the new Hypericum.

The photograph on the first sheet comprises a side perspective view of a plant of 'Bright Blossom' with flowers and fruits.

The photograph at the top of the second sheet is a close-up view of a typical plant of 'Bright Blossom'.

The photograph at the bottom of the second sheet comprises a side perspective view of a typical flowering stem of 'Bright Blossom' in fruit.

DETAILED BOTANICAL DESCRIPTION

The new Hypericum has not been observed under all possible environmental conditions. The phenotype may vary somewhat with variations in environment such as temperature, daylength and light intensity, without, however, any variance in genotype.

The aforementioned photographs, following observations and measurements describe plants grown in Burgh Haamstede, The Netherlands, in a polyethylene-covered structure and under commercial production practices. Plants were grown in 21-cm containers and were about three years old. During the production of the plants, the average day temperature was about 20° C. and average night temperature was about 13° C. In the following description, color references are made to The Royal Horticultural Society Colour Chart, 2001 Edition, except where general terms of ordinary dictionary significance are used.

Botanical classification: *Hypericum androsaemum* cultivar Bright Blossom.

Parentage: Naturally-occurring whole plant mutation of *Hypericum androsaemum* cultivar Autumn Blaze, not patented.

Propagation:

*Type.*—Terminal cuttings.

*Time to initiate roots.*—About two to three weeks at 20° C.

*Time to produce a rooted cutting.*—About two to three months at 20° C.

*Root description.*—Fine; white in color.

*Rooting habit.*—Freely branching, dense.

Plant description:

*Plant form.*—Upright and outwardly spreading perennial woody shrub; globular to broadly globular in shape.

*Growth habit.*—Moderately vigorous. Freely basal branching; dense and bushy growth habit.

*Plant height.*—About 60 to 70 cm.

*Plant width* (*spread*).—About 70 to 75 cm.

*Quantity of stems per year.*—About 40.

*Lateral branches.*—Quantity per plant: About 25. Length: About 60 to 70 cm. Diameter: About 5 to 10 mm. Internode length: About 5 to 6 cm. Strength: Strong. Texture: Leathery, smooth, glabrous. Color: Young: 145A. Woody: 174A.

*Foliage description.*—Leaves opposite, decussate; single; sessile and generally symmetrical. Length: About 4.5 to 6 cm. Width: About 3.5 to 4.2 cm. Shape: Cordate. Apex: Rounded. Base: Cordate. Margin: Entire. Texture: Leathery, glabrous. Venation pattern: Pinnate. Color: Developing leaves, upper surface: 144A. Developing leaves, lower surface: 146D. Fully expanded leaves, upper surface: 147A. Fully expanded leaves, lower surface: 147B. Venation, upper surface: 146C. Venation, lower surface: 146D.

Flower description:

*Flower type and habit.*—Bright yellow single flowers arranged in terminal compound umbels with about 13 to 16 flowers per lateral branch. Flowers not fragrant. Flowers not persistent. Flowers upright.

*Natural flowering season.*—Summer and fall in Burgh Haamstede, The Netherlands; flowering period typically lasts about 60 days.

*Postproduction longevity.*—Cut stems are typically harvested when all flowers have developed fruits. Postproduction longevity of cut stems with fruits is about three weeks.

*Inflorescence height.*—About 6 to 7 cm.

*Inflorescence diameter.*—About 5 to 6 cm.

*Flower buds.*—Height: About 7 to 9 mm. Diameter: About 4 to 5 mm. Shape: Ovoid. Color: 162A.

*Flowers.*—Diameter: About 3 cm. Depth: About 1.8 cm.

*Petals.*—Quantity per flower: Five. Length: About 1.2 to 1.4 cm. Width: About 5 to 7 mm. Shape: Elliptic. Aspect: Concave. Apex: Emarginate. Base: Attenuate. Margin: Entire. Texture, upper and lower surfaces: Smooth, glabrous; satiny. Color: Developing and fully expanded petals, upper surface: 13B; color fading to 13C with subsequent development. Developing and fully expanded petals, lower surface: 12B.

*Sepals.*—Quantity per flower: Five. Length: About 6 to 8 mm. Width: About 3 to 6 mm. Shape: Oblong. Apex: Acute. Base: Cuneate. Margin: Entire. Texture, upper and lower surfaces: Smooth, glabrous. Color: Developing and fully expanded sepals, upper surface: 146C. Developing and fully expanded sepals, lower surface: 146D.

*Peduncles.*—Length: About 1.5 to 2 cm. Diameter: About 2 to 3 mm. Orientation: Erect to about 45° from vertical. Strength: Moderately strong. Color: 175A.

*Reproductive organs.*—Stamens: Quantity per flower: About 45. Anther shape: Rounded. Anther length: About 0.5 mm. Anther color: 17A. Pollen amount: Moderate to abundant. Pollen color: 15A. Pistils: Quantity per flower: Three. Pistil length: About 6 to 7 mm. Stigma shape: Rounded. Stigma color: 173A. Style length: About 6 to 7 mm. Style color: 3C. Ovary color: 2D.

*Fruits.*—Quantity per flower: One. Days to ripening: About six. Longevity on the plant: About three weeks. Type: Capsule. Shape: Ellipsoidal. Length: About 7 to 8 mm. Diameter: About 6 to 7 mm. Texture: Smooth, glabrous. Color: 53B.

*Seeds.*—Quantity per fruit: More than 100. Length: Less than 1 mm. Diameter: Less than 1 mm. Texture: Smooth, glabrous. Color: Close to 199C.

Disease/pest resistance: Plants of the new Hypericum have not been observed to be resistant to pathogens and pests common to Hypericum.

Temperature tolerance: plants of the new Hypericum have been observed to tolerate temperatures ranging from about 0 to 40° C.

It is claimed:

1. A new and distinct cultivar of Hypericum plant named 'Bright Blossom', as illustrated and described.

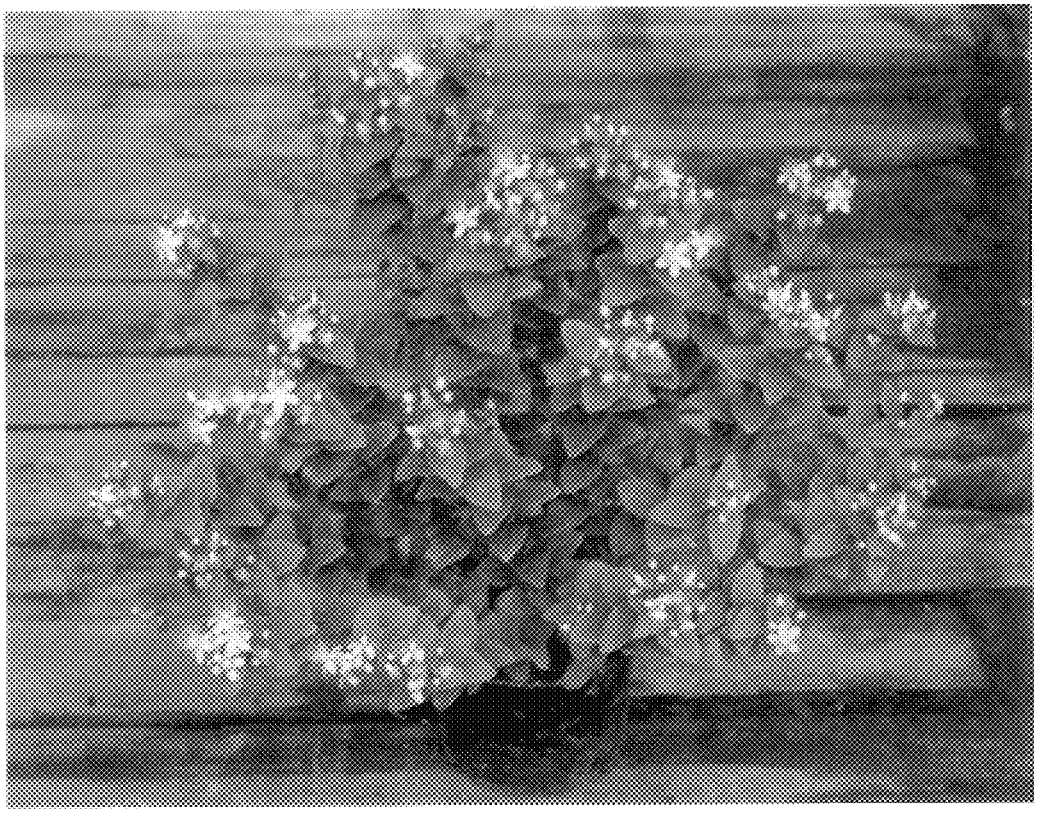

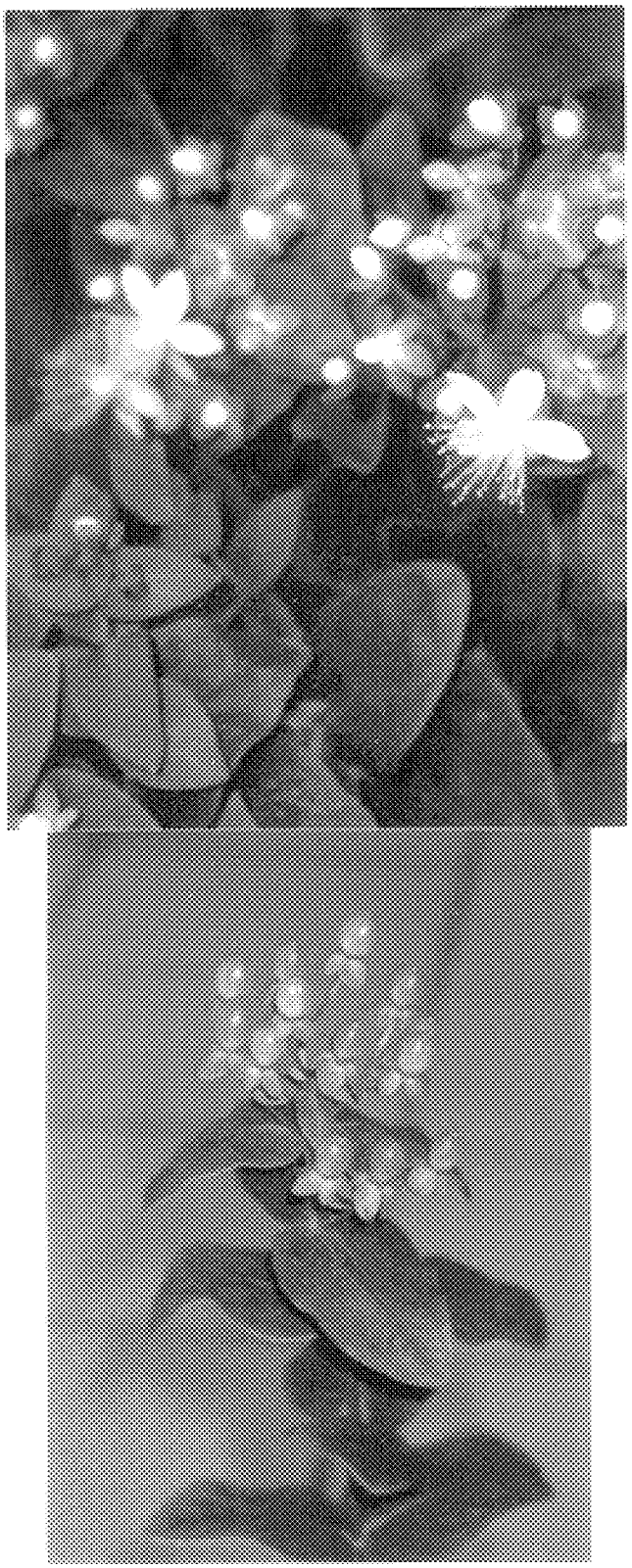

* * * * *